United States Patent [19]

Goodman, Jr. et al.

[11] Patent Number: 5,158,819
[45] Date of Patent: Oct. 27, 1992

[54] POLYMERIC WEB EXHIBITING A SOFT, SILKY, CLOTH-LIKE TACTILE IMPRESSION AND INCLUDING A CONTRASTING VISUALLY DISCERNIBLE PATTERN HAVING AN EMBOSSED APPEARANCE ON AT LEAST ONE SURFACE THEREOF

[75] Inventors: William H. Goodman, Jr.; William I. Mullane, Jr.; Bruce F. Perry; Gary G. Trout, all of Cincinnati, Ohio

[73] Assignee: The Procter & Gamble Company, Cincinnati, Ohio

[21] Appl. No.: 546,163

[22] Filed: Jun. 29, 1990

[51] Int. Cl.⁵ .............................. B32B 3/10
[52] U.S. Cl. .................... 428/131; 428/124; 428/147; 428/141; 428/119; 428/156; 428/172; 428/195; 428/409; 264/154; 264/504; 264/557; 264/570; 604/366; 604/378; 604/385.1
[58] Field of Search .......... 428/124, 131, 137, 138, 428/147, 119, 120, 141, 156, 172, 179, 195, 409; 264/154, 504, 570, 557; 604/366, 385.1, 378

[56] References Cited

U.S. PATENT DOCUMENTS

| | | | |
|---|---|---|---|
| D. 305,181 | 12/1989 | Veith | D5/53 |
| D. 305,182 | 12/1989 | Peddada et al. | D5/53 |
| 3,929,135 | 12/1975 | Thompson | 128/287 |
| 3,952,745 | 4/1976 | Duncan | 128/287 |
| 3,989,867 | 11/1976 | Sisson | 428/132 |
| 4,151,240 | 4/1979 | Lucas et al. | 264/504 |
| 4,233,017 | 11/1980 | Lucas et al. | 425/290 |
| 4,259,286 | 3/1981 | Louis et al. | 264/555 |
| 4,327,730 | 5/1982 | Sorensen | 128/287 |
| 4,333,979 | 6/1982 | Sciaraffa et al. | 428/179 |
| 4,342,314 | 8/1982 | Radel et al. | 128/287 |
| 4,395,215 | 7/1983 | Bishop | 425/290 |
| 4,463,045 | 7/1984 | Ahr et al. | 428/131 |
| 4,463,049 | 7/1984 | Kracke | 428/281 |
| 4,552,709 | 11/1985 | Koger, II et al. | 264/504 |
| 4,591,523 | 5/1986 | Thompson | 428/131 |
| 4,609,518 | 9/1986 | Curro et al. | 264/504 |
| 4,629,643 | 12/1986 | Curro et al. | 428/131 |
| 4,637,819 | 1/1987 | Ouellette et al. | 604/369 |
| 4,681,793 | 7/1987 | Linman et al. | 428/138 |
| 4,695,422 | 9/1987 | Curro et al. | 264/504 |
| 4,704,112 | 11/1987 | Suzuki et al. | 604/378 |
| 4,747,991 | 5/1988 | Bishop | 264/504 |
| 4,772,444 | 9/1988 | Curro et al. | 264/557 |
| 4,778,644 | 10/1988 | Curro et al. | 264/557 |
| 4,781,710 | 11/1988 | Megison et al. | 604/378 |
| 4,846,821 | 7/1989 | Lyons et al. | 604/369 |
| 4,859,519 | 8/1989 | Cabe, Jr. et al. | 428/131 |

*Primary Examiner*—Ellis P. Robinson
*Assistant Examiner*—J. Weddington
*Attorney, Agent, or Firm*—E. Kelly Linman; Thomas H. O'Flaherty; Michael E. Hilton

[57] ABSTRACT

A soft, silky, cloth-like polymeric web exhibiting either patterns of microapertured or microbubbled surface aberrations, said webs further including a contrasting visually discernible pattern which imparts an embossed appearance to at least one surface thereof. Such polymeric webs may be either fluid-pervious or fluid-impervious, as desired, depending upon the particular end use. In a particularly preferred embodiment, the visually discernible pattern comprises a regularly repeating pattern which imparts an improved aesthetic appearance to the webs. Method and apparatus for producing such polymeric webs are also disclosed.

26 Claims, 14 Drawing Sheets

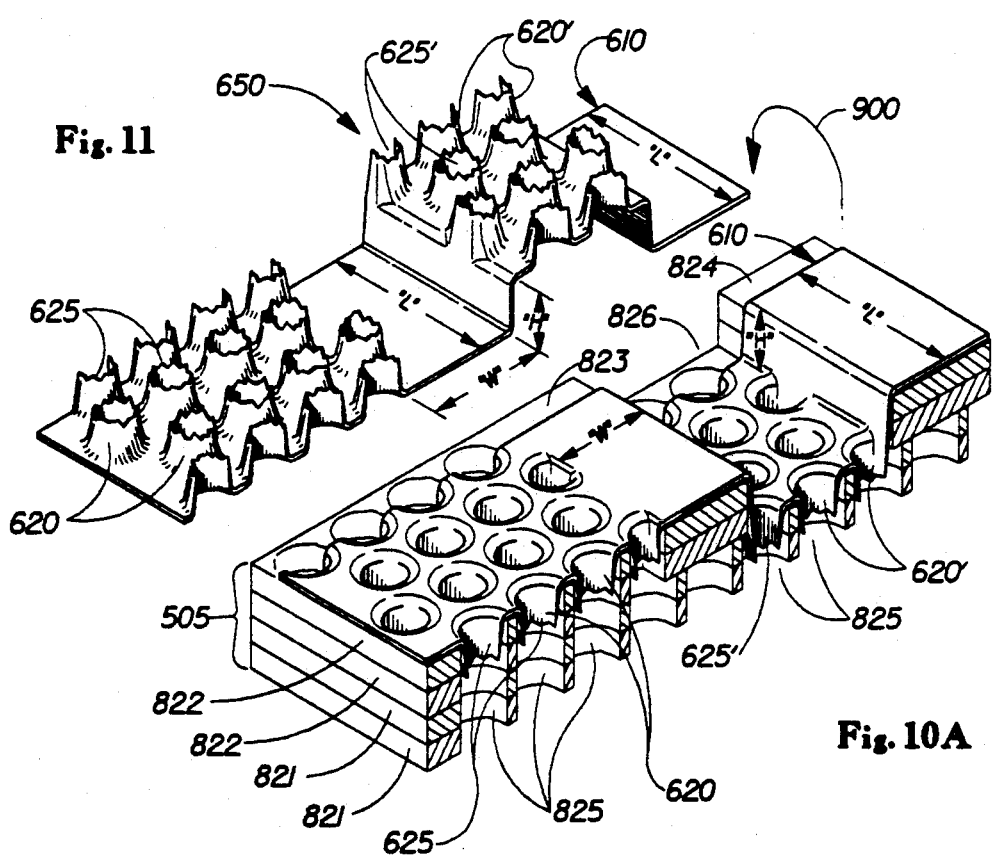

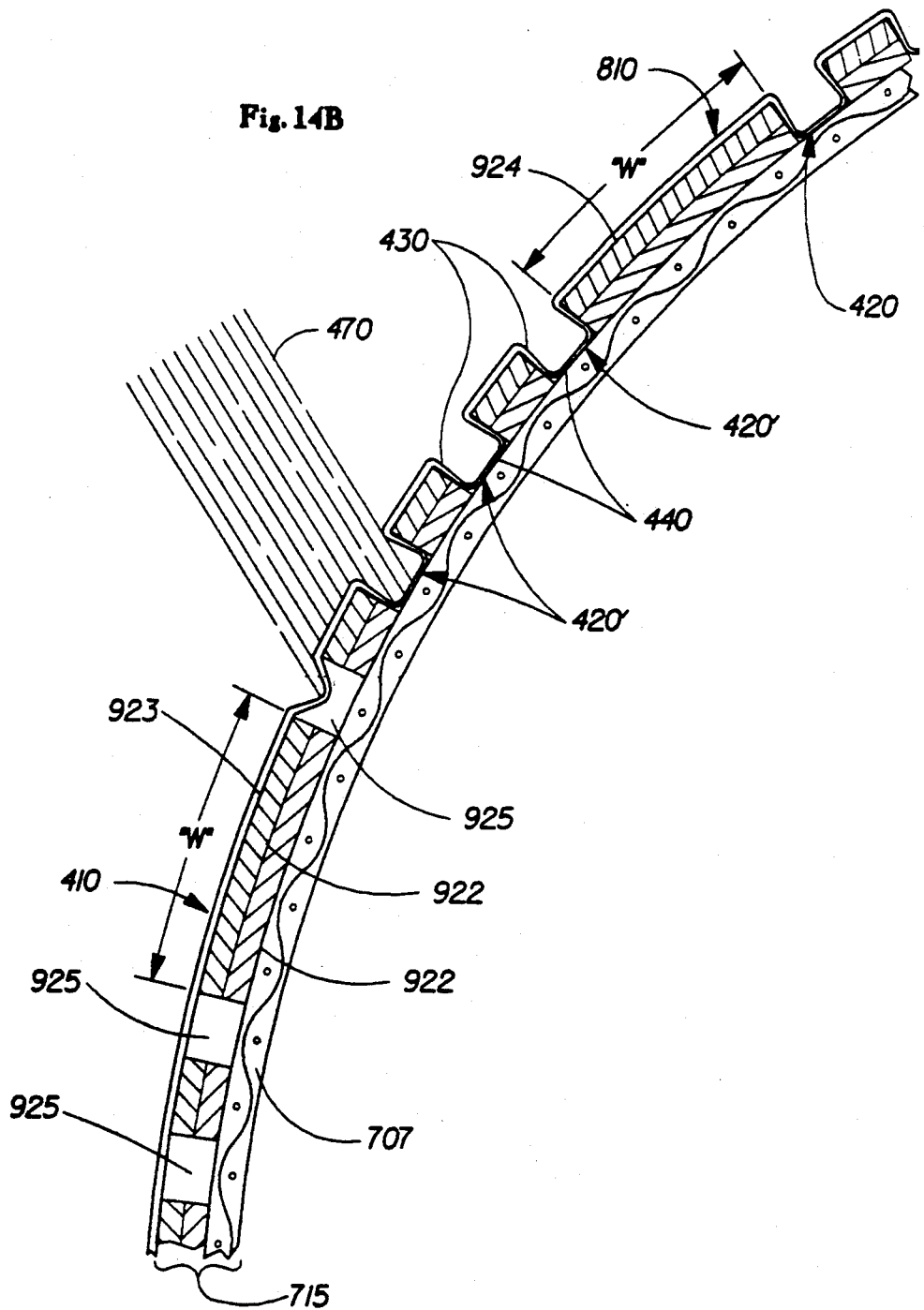

POLYMERIC WEB EXHIBITING A SOFT, SILKY, CLOTH-LIKE TACTILE IMPRESSION AND INCLUDING A CONTRASTING VISUALLY DISCERNIBLE PATTERN HAVING AN EMBOSSED APPEARANCE ON AT LEAST ONE SURFACE THEREOF

TECHNICAL FIELD

The present invention relates to improvements in soft and silky microapertured polymeric webs of the type generally disclosed in commonly assigned U.S. Pat. No. 4,629,643 issued to Curro et al. on Dec. 16, 1986 and U.S. Pat. No. 4,681,793 issued to Linman et al. on Jul. 21, 1987 as well as to improvements in soft and cloth-like microbubbled polymeric webs of the type generally disclosed in commonly assigned U. S. Pat. No. 4,846,821 issued to Lyons et al. on Jul. 11, 1989, all of said patents being hereby incorporated herein by reference.

The present invention has further relation to improvements wherein webs of the aforementioned types retain their soft, silky, cloth-like tactile and visual attributes, which are highly preferred when such webs contact the user's skin, while further enhancing the appearance of said webs by imparting a contrasting visually discernible pattern having an embossed appearance thereto.

The contrasting visually discernible pattern may be employed to improve the aesthetics of the polymeric webs in question by imparting a decorative ornamental appearance thereto or it may be employed to apply graphical indicia, such as usage instructions, directly onto the webs in question.

Improved polymeric webs of the present invention may be either fluid-pervious or fluid-impervious, depending upon the desired end use. Fluid-impervious webs of the present invention are particularly desirable for use as backsheets in single-use absorbent structures such as diapers, incontinence briefs, catamenial pads and the like.

Other readily envisioned uses for webs of the present invention include flexible packaging applications, articles of wearing apparel, bed pads, coverings for upholstered articles such as furniture cushions and the like.

BACKGROUND OF THE INVENTION

Absorptive devices, such as diapers, catamenial pads, bed pads, incontinence briefs and the like are well known. These devices are used to absorb liquid from the human body and retain that liquid within an underlying absorbent core. It is also known to cover the exterior of these devices with a flexible, plastic backsheet to prevent the liquid absorbed into the core from striking through the absorptive device and soiling other adjacent clothing, such as bedding and wearing apparel. Although such waterproof plastic backsheets of the prior ar are highly effective in preventing strikethrough and in helping to contain the liquid within the absorptive device, they typically tend to be uncomfortable to wear when they make sustained contact with the skin. In addition, they often make embarrassing "rattling" or "rustling" noises when subjected to movement as a result of the wearer's normal body movements.

Great strides have been made in overcoming many of the negatives associated with such prior art fluid-impervious polymeric webs, particularly when they are employed as fluid-impervious backsheets in single use absorbent structures. Commonly assigned U.S. Pat. No. 4,681,793 issued to Linman et al. on Jul. 21, 1987 and incorporated herein by reference disclosed a particularly preferred non-occluding, liquid-impervious, composite backsheet for such absorptive devices. The backsheet disclosed in the aforementioned Linman et al. patent comprises a combination of two layers. The first layer, which does not contact the wearer's skin, is preferably comprised of a liquid-impervious polymeric film or a liquid-impervious coating. The second layer is preferably comprised of a polymeric film which has been made pervious to liquid by providing a multiplicity of relatively small protuberances, each ending in a tiny aperture, i.e., a microaperture, substantially across its entire surface. The microapertured protuberances, which resemble a tiny volcano in cross-section, exhibit a soft, highly preferred tactile impression which is sometimes characterized as "silky". Details of the second microapertured layer of the composite backsheet employed in the composite structure disclosed in commonly assigned U.S. Pat. No. 4,681,793 to Linman et al. are fully set forth in commonly assigned U.S. Pat. No. 4,629,643 issued to Curro et al. on Dec. 16, 1986, which patient is also incorporated herein by reference. The second microapertured layer in composite structures of the type disclosed in the aforementioned Linman et al. patient is oriented in use so that the tiny volcano-like cusps of the second layer constitute the exposed portion of the backsheet. Thus the second layer minimize the area of contact between the composite backsheet and the wearer's skin, while the first layer or coating renders the composite backsheet impervious to the passage of fluid.

Still another polymeric web material which has been found particularly suitable for use as a liquid-impervious backsheet in single-use structures such as diapers, sanitary napkins, etc. is disclosed in commonly assigned U.S. Pat. No. 4,846,821 issued to Lyons et al. on Jul. 11, 1989 and incorporated herein by reference. The Lyons et al. patent disclosed a microbubbled, substantially fluid-impervious polymeric web which exhibits a soft and cloth-like tactile impression as well as a low noise generation characteristic previously achievable only in fluid-pervious microapertured webs of the type disclosed in the aforementioned commonly assigned U.S. Pat. No. 4,629,643 to Curro et al. However, because each of the surface aberrations in the web of Lyons et al. exhibits an unruptured microbubble rather than a microaperture at its tip, the web of Lyons et al. remains substantially fluid-impervious. Accordingly, there is no need to provide either an additional fluid-impervious layer of polymeric film or to apply a fluid-impervious coating to the microbubbled web of Lyons et al. to render it substantially fluid-impervious.

Experience to date has demonstrated that consumers strongly prefer the soft, silky, cloth-like characteristics of microapertured and microbubbled polymeric webs of the type disclosed in the aforementioned commonly assigned patents to Lyons et al., Curro et al. and Linman et al. over substantially smooth surfaced polymeric webs of the type generally disclosed in the prior art, particularly in applications where the web ib intended to make sustained contact with the skin.

However, Applicants have unexpectedly discovered that the strong consumer preference for webs of the type disclosed in the aforementioned commonly assigned patents to Lyons et al., Curro et al. and Linman et al. can be enhanced even further by incorporating a contrasting visually discernible pattern which imparts an embossed appearance to the surface of such microapertured and microbubbled webs.

OBJECTS OF THE INVENTION

Accordingly, it is an object of the present invention to provide soft, silky, cloth-like polymeric webs exhibiting either patterns of microapertured or microbubbled surface aberrations, as generally taught by the aforementioned commonly assigned patents to Linman et al., Curro et al. and Lyons et al., said webs further including a contrasting visually discernible pattern which imparts an embossed appearance to at least one surface thereof.

It is another object of the present invention to provide such polymeric webs which may be either fluid-pervious or fluid-impervious, as desired, depending upon the particular end use.

It is another object of the present invention to provide such polymeric webs, wherein said contrasting visually discernible pattern comprises a regularly repeating pattern.

It is another object of the present invention to provide such polymeric webs, wherein the contrasting visually discernible pattern imparts an improved aesthetic appearance to the webs.

It is still another object of the present invention to provide method and apparatus for producing such polymeric webs exhibiting a contrasting visually discernible pattern in at least one of their surfaces.

DISCLOSURE OF THE INVENTION

In a particularly preferred embodiment, the present invention comprises a microapertured polymeric web exhibiting a soft and silky tactile impression as well as a contrasting visually discernible pattern imparting an embossed appearance to at least one of its surfaces. As generally disclosed in commonly assigned U.S. Pat. No. 4,629,643 issued to Curro et al. on Dec. 16, 1986, the silky feeling surface of the web comprises a pattern of discrete volcano-like surface aberrations which are not individually discernible to the normal naked eye when the perpendicular distance between the web and the observer's eye is at least about 12 inches. The end of each of the surface aberrations further includes at least one tiny aperture. i.e., a microaperture, which substantially coincides with the surface aberrations's point of maximum amplitude. The microaperture further exhibits a multiplicity of thin, irregularly shaped petals about its periphery, thereby creating a discontinuity which reduces the resistance to compression and shear of each of the surface aberrations as well as the degree of contact with the observer's skin. As a result, the overall tactile impression of the web is perceived as generally soft and silky.

The web further includes a contrasting visually discernible pattern having an embossed appearance, said pattern comprising a substantially planar, non-microapertured portion of the web located in the plane in which at least a portion of the surface aberrations originate. The substantially planar, non-microapertured portion of the web has a width "W" equal to at least about 1½ times the normal center-to-center distance between adjacent surface aberrations, as measured in the microapertured portions of the web in the immediate vicinity of the visually discernible pattern. The substantially planar, non-microapertured portion of the web also has a length "L" extending continuously in a direction substantially perpendicular to its width. The width "W" and length "L" together define a contrasting pattern which imparts an embossed appearance to the web and which is visually discernible to the normal naked eye when the perpendicular distance between the observer's eye and the plane of the web is about 12 inches.

In a particularly preferred embodiment, the continuously extending length "L" of the substantially planar, non-microapertured portion of the web forms a halo or border comprising at least one closed loop so as to completely isolate the surface aberrations contained within the loop from the surface aberrations surrounding the loop. In a particularly preferred embodiment, the visually discernible pattern comprises a multiplicity of such closed loops and is arrayed in a regularly repeating ornamental design.

If desired, the embossed appearance can be further enhanced by positioning the surface aberrations contained within the closed loop or loops in a plane remote from the surrounding surface aberrations. In a particularly preferred embodiment, the surface aberrations contained within the closed loop originate in a plane located at a higher elevation than the plane of the surface aberrations surrounding the closed loop. Most preferably the planes are separated from one another by a distance equal to at least 1.0 times the amplitude of the surface aberrations surrounding the closed loop to maximize the embossed appearance of the web.

In a particularly preferred embodiment, the substantially planar, non-microapertured portion of the web comprising the contrasting visually discernible pattern is substantially smooth and will produce reflective gloss highlights which direct the observer's attention to the pattern imparted to the web when the web is struck by incident light rays.

If the microapertured web is to be employed in an application where fluid-imperviousness is required, e.g., as in a diaper backsheet, a substantially liquid-impervious layer or coating can be secured in juxtaposed relation adjacent the non-exposed surface of the web, as generally taught by commonly assigned U.S. Pat. No. 4,681,793 issued to Linman et al. on Jul. 21, 1987. This layer or coating renders the resulting composite structure substantially impervious to the passage of fluid without destroying the highly preferred tactile impression produced by the exposed tips of the microapertured surface aberrations.

Alternatively, the visually discernible pattern of the present invention may be employed with microbubbled, substantially fluid-impervious polymeric webs of the type disclosed in commonly assigned U.S. Pat. No. 4,846,821 issued to Lyons et al. on Jul. 11, 1989. In the latter case, there is no need to provide a second fluid-impervious layer or coating to render the web substantially impervious to fluid.

If desired, polymeric webs of the present invention may also exhibit a combination of microbubbled and microapertured surface aberrations. In this case only the microapertured portions of the web will be fluid-pervious.

In still another embodiment of the present invention, polymeric webs exhibiting only microapertured surface aberrations may be provided with a patterned secondary fluid-impervious layer or coating secured adjacent the non-exposed surface of the web to render predetermined portions of the microapertured web substantially impervious to the passage of fluid.

BRIEF DESCRIPTION OF THE DRAWINGS

While the specification concludes with claims particularly pointing out and distinctly claiming the present invention, it is believed the present invention will be better understood from the following description in which:

FIG. 10A is a highly enlarged simplified, perspective view of a segment of the forming structure and film shown in FIG. 9 taken at a point corresponding to inset 10A in FIG. 9, said forming structure being shown in a planar rather its true arcuate condition for ease of illustration;

FIG. 11 is a simplified perspective view of the film shown in FIG. 10A after it has been removed from the forming structure and inverted, as generally shown by the arrow 900 connecting FIGS. 10A and 11 with one another;

FIG. 14B is a highly enlarged, simplified cross-sectional illustration of the web forming process of FIG. 14 taken at a point corresponding to inset 14B in FIG. 14;

DETAILED DESCRIPTION OF THE INVENTION

While the present invention will be described in the context of providing a "quiet", substantially fluid-impervious, polymeric single use diaper backsheet exhibiting a cloth-like visual and tactile impression as well as a visually discernible pattern having an embossed appearance on its exposed surface, the present invention is in no way limited to such application. The present invention may be practiced with equal facility to produce fluid-pervious polymeric webs exhibiting such desirable characteristics. The detailed description contained herein, which relates to particularly preferred structures and their use as fluid-impervious backsheets in single use diapers, will allow one skilled in the art to readily adapt the invention to other devices.

Figure 1:
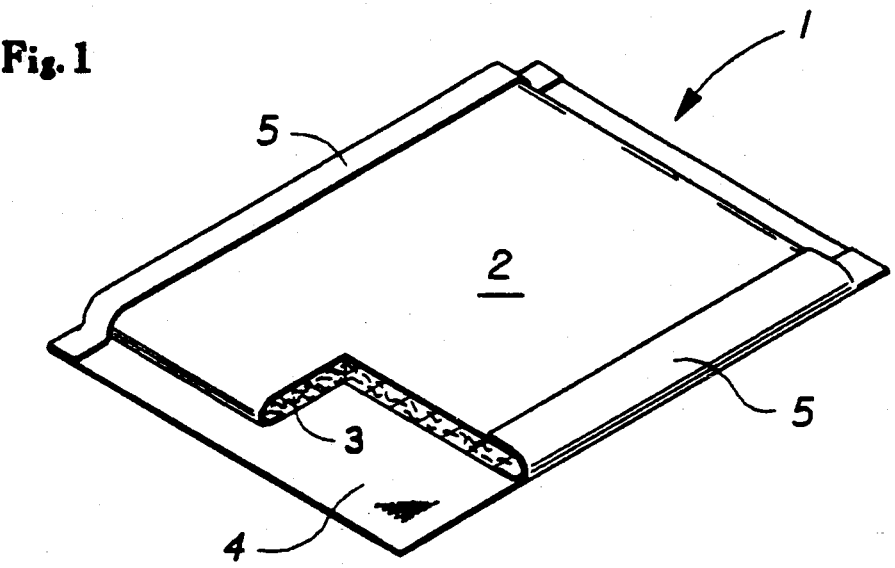
FIG. 1 is a simplified perspective illustration of a single use diaper employing a fluid-impervious composite backsheet of the present invention.

FIG. 1 is a simplified perspective view of a single use absorbent bandage comprising a diaper in an unfolded condition. Various layers have been cut away to more clearly show the structural details of this embodiment. The single use diaper is referred to generally by the reference numeral 1. A fluid-pervious topsheet is shown as 2. The other two major components of the single use diaper 1 are the absorbent element or pad 3 and a substantially fluid-impervious backsheet 4 of the present invention. In general, the side flaps 5 of the backsheet 4 are folded up so as to cover the edges of the absorbent pad 3 and topsheet 2. Topsheet 2 is generally folded to completely enclose the ends of the absorbent pad 3. As will be appreciated by those skilled in the art, the drawing of single use diaper 1 in FIG. 1 is a simplified representation. A more detailed description of a preferred embodiment of a single use diaper is contained in commonly assigned U.S. Pat. No. 3,952,745 issued to Duncan on Apr. 27, 1976, said patent being hereby incorporated herein by reference. As will also be appreciated by those skilled in the art, topsheet 2 of the single use diaper 1 shown in FIG. 1 is normally oriented so as to contact the wearer's body in use, i.e., the topsheet side is considered to be the wearer contacting surface of the diaper.

Figure 2:
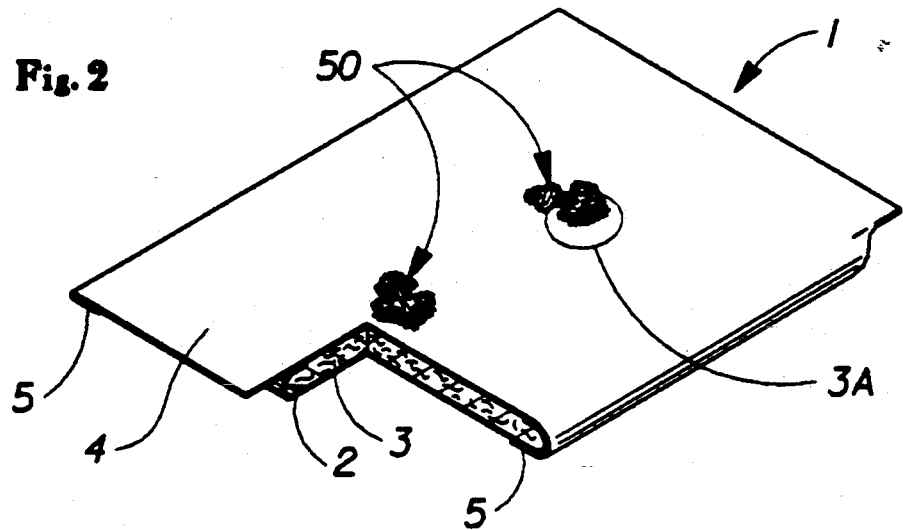
FIG. 2 is a view of the diaper shown in FIG. 1 after the diaper has been inverted to better reveal the visually discernible decorative pattern present on the exposed surface of the composite backsheet.

FIG. 2 is a perspective view of the single use diaper 1 generally shown in FIG. 1 taken from the non-wearer contacting or backsheet surface thereof. Although it is clear that there will be some contact with the wearer's skin by the overlapping side flaps 5 of the backsheet, the bulk of the exposed area of the backsheet 4 is outwardly directed away from the wearer's skin in use. Accordingly, most contact between the exposed surface of the backsheet 4 and the wearer's skin will be made when the diaper 1 is being applied to the torso of the wearer. In the case of an infant diaper, contact will most likely be with the hands of the person applying the diaper or holding the infant, while in the case of an adult incontinence diaper, the contact during application will most likely be with the hands of the wearer. In either case, it is generally desirable that the visual and tactile impression of the exposed surface of the backsheet 4 be as pleasant as possible. In most instances, a cloth-like visual and tactile impression are perceived as desirable, particularly when there is lateral movement between the user's skin and the backsheet.

Another highly desirable attribute for a fluid-impervious backsheet in a single use absorbent bandage is that the web not make "rattling" or "rustling" sounds when subjected to movement. The latter characteristic is particularly important when fluid-impervious webs are employed in adult incontinence devices, such as diapers, since the "rustling" or "rattling" noises generated by normal body movements can be extremely embarrassing to the wearer.

In the diaper embodiment 1 illustrated in FIGS. 1 and 2, backsheet 4 is preferably comprised of a "quiet", substantially fluid-impervious composite structure of the type generally disclosed in commonly assigned U.S. Pat. No. 4,681,793 issued to Linman et al. on Jul. 21, 1987 and incorporated herein by reference. However, as can be seen from FIG. 2, the outermost or exposed layer of the composite diaper backsheet 4 includes a decorative pattern comprising, for example, a multiplicity of boat anchors 50. The particular decorative pattern employed can, if desired, be selected to be gender specific for the particular product. For example a nautical pattern comprising a multiplicity of boat anchors 50 might be selected for products intended for boys, while a floral or lace pattern (not shown) might be selected for use on products intended for girls.

Figure 3A:
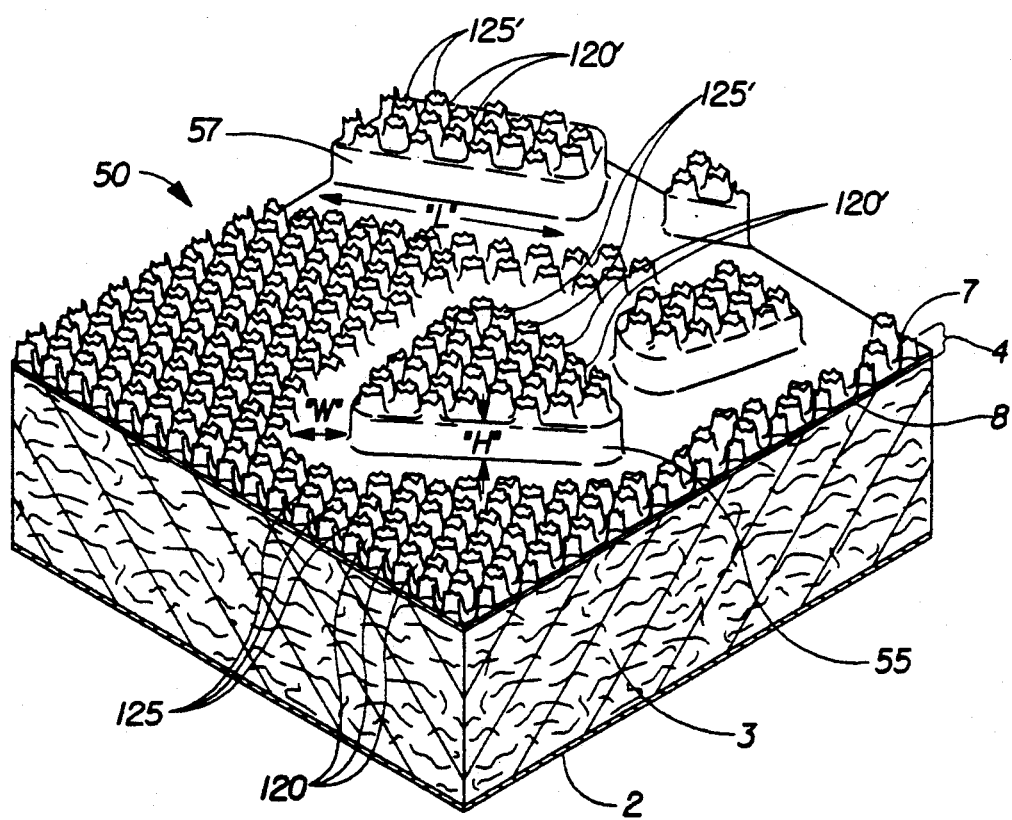
FIG. 3A is a greatly enlarged segment taken at a point corresponding to inset 3A in FIG. 2, said inset revealing the visually discernible pattern on the composite backsheet in much greater detail.

FIG. 3A is a greatly enlarged segment of the diaper shown in FIGS. 1 and 2, said segment being taken at a point corresponding to inset 3A in FIG. 2. The outermost or exposed layer of composite backsheet 4 shown in FIG. 3 comprises a microapertured web 7 including a pattern of surface aberrations 120, which are not individually discernible to the normal naked eye when the perpendicular distance between the plane of the web and the observer's eye is at least about 12 inches, extending across a substantial portion of its surface. Each surface aberration 120 exhibits a tiny volcano-shaped aperture. i.e., microaperture 125, coinciding substantially with its maximum amplitude. Adjacent the microapertured polymeric web 7 there is provided a fluid-impervious layer or coating 8 which renders the microapertured surface aberrations 120 in web 7 substantially impervious to the passage of fluid.

As can also be seen in the greatly enlarged segment of FIG. 3A, the visually discernible pattern of boat anchors 50 is made up of a substantially planar, non-microapertured, horizontally oriented portion of polymeric web 7. The substantially planar portion of the web exhibits a width "W" equal to at least about 1½ times the normal center to center distance between adjacent surface aberrations 120, as measured in the microapertured portions of the web 7 in the immediate vicinity of the visually discernible boat anchor pattern. The substantially planar portion of the web further exhibits a length "L", which extends continuously in a direction substantially perpendicular to its width "W". Together the width "W" and length "L" define a contrasting pattern which has an embossed appearance and which is visually discernible to the normal naked eye when the perpendicular distance between the observer's eye and the plane of the web is about 12 inches. As can be seen from FIG. 3A, the width "W" may be constant or may vary, as desired, along the length "L" of the pattern.

The substantially planar portion of the web of width "W" and length "L" may be used to provide graphical indicia, such as usage instructions, on the surface of the web or it may be used to enhance the aesthetics of the web.

To maximize the discernibility of the pattern created in microapertured and microbubbled webs of the present invention, the non-microapertured or non-microbubbled portions of the web comprising the contrasting visually discernible pattern are preferably substantially smooth so that they will produce a reflective gloss/highlight when struck by incident light rays. Conversely, if a non-glossy halo or border is preferred, the substantially planar, non-microapertured or non-microbubbled horizontally oriented portions of the web may be provided with a regularly spaced, microscopic pattern of surface aberrations of the type generally disclosed in commonly assigned U.S. Pat. No. 4,463,049 issued to Ahr et al. on Jul. 31, 1984 and hereby incorporated herein by reference. The visual discernibility of the pattern in webs of the present invention will, in general, increase as the contrast between the patterned and the unpatterned portions of the web, either in terms of gloss or texture, increases.

In the particularly preferred microapertured web embodiment 7 illustrated in FIG. 3A, the length "L" of the substantially planar, non-microapertured portion of the web forms a halo or border comprising at least one closed loop, such as at anchor tip 55, to completely isolate the microapertured surface aberrations 120' contained within the loop from the otherwise identical microapertured surface aberrations 120 surrounding the loop. In a particularly preferred embodiment, the contrasting visually discernible pattern comprises a multiplicity of such closed loops, e.g., anchor tip 55, central anchor portion 57, etc. In such case the surface aberrations 120' contained within one closed loop are isolated not only from the surrounding surface aberrations 120, but also from the surface aberrations 120' contained within adjacent closed loops.

The surface aberrations 120' contained within the isolated loop or loops may be of the same or of a dissimilar size from the surface aberrations 120 surrounding the loop.

Also, if desired, the surface aberrations 120' contained within the loop may be located in a plane remote from the plane of the surface aberrations 120 surrounding the loop or loops, thereby further enhancing the embossed appearance of the contrasting visually discernible pattern in the web.

In the microapertured web embodiment 7 shown in FIG. 3A, the microapertured surface aberrations 120' contained within closed loops 55 and 57 are located in a plane above the plane of the surface aberrations 120 surrounding the closed loops. To maximize the embossed appearance of the web, the plane containing surface aberrations 120' located within the closed loops is preferably separated from the plane containing the surrounding surface aberrations 120 by a distance equal to at least about 1.0 times the amplitude of the surface aberrations 120 surrounding the closed loops.

Separating the plane containing surface aberrations 120' from the plane containing surface aberrations 120 surrounding the loops enhances the embossed appearance of the web for several reasons. First, separating the plane of the surface aberrations 120' contained within the closed loops from the plane of the surrounding surface aberrations 120 accentuates the three-dimensionality of the web's surface. Second, the smooth surface of the resulting vertical wall having a height "H" which separates the plane of surface aberrations 120' contained within the closed loops from the plane of the surrounding surface aberrations 120 also produces a reflective gloss highlight when struck by non-perpendicular incident light rays. Finally, the vertical wall having a height "H" also casts a shadow when struck by non-perpendicular incident light rays, thereby further accentuating the non-planar condition of the microapertured polymeric web 7.

As will be appreciated by those skilled in the art, the surface aberrations 120' contained within closed loops 55, 57, etc., could, if desired, originate in a plane located below the plane of the surrounding surface aberrations 120 rather than in a plane located above the surrounding surface aberrations. In the latter case the vertical wall of height "H" separating the two planes is preferably positioned immediately adjacent the surrounding surface aberrations 120 rather than immediately adjacent the depressed surface aberrations 120' contained within the closed loops 55, 57, etc.

Figure 4:
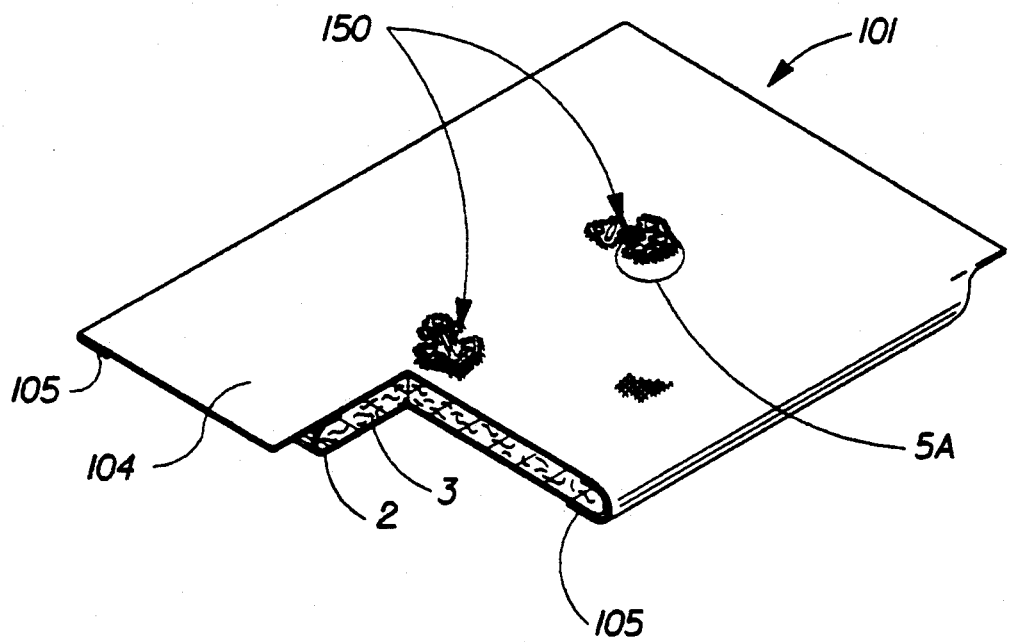
FIG. 4 is a simplified perspective view of another single use diaper employing an alternative fluid-impervious backsheet of the present invention.

FIG. 4 disclosed another single use diaper embodiment 101 having an absorbent core 3, a fluid-pervious topsheet 2 and a microbubbled fluid-impervious backsheet 104 of the present invention. Like diaper embodiment 1, the longitudinal edges 105 of fluid-impervious backsheet 104 are folded over the liquid-pervious topsheet 2 in a manner generally similar to that illustrated in FIGS. 1 and 2. Like composite backsheet 4 shown in FIGS. 2 and 3A, microbubbled fluid-impervious backsheet 104 of the present invention includes a visually discernible pattern of boat anchors 150, which are generally similar to boat anchors 50 employed in the outermost or exposed layer 7 of the composite backsheet 4.

Figure 5A:
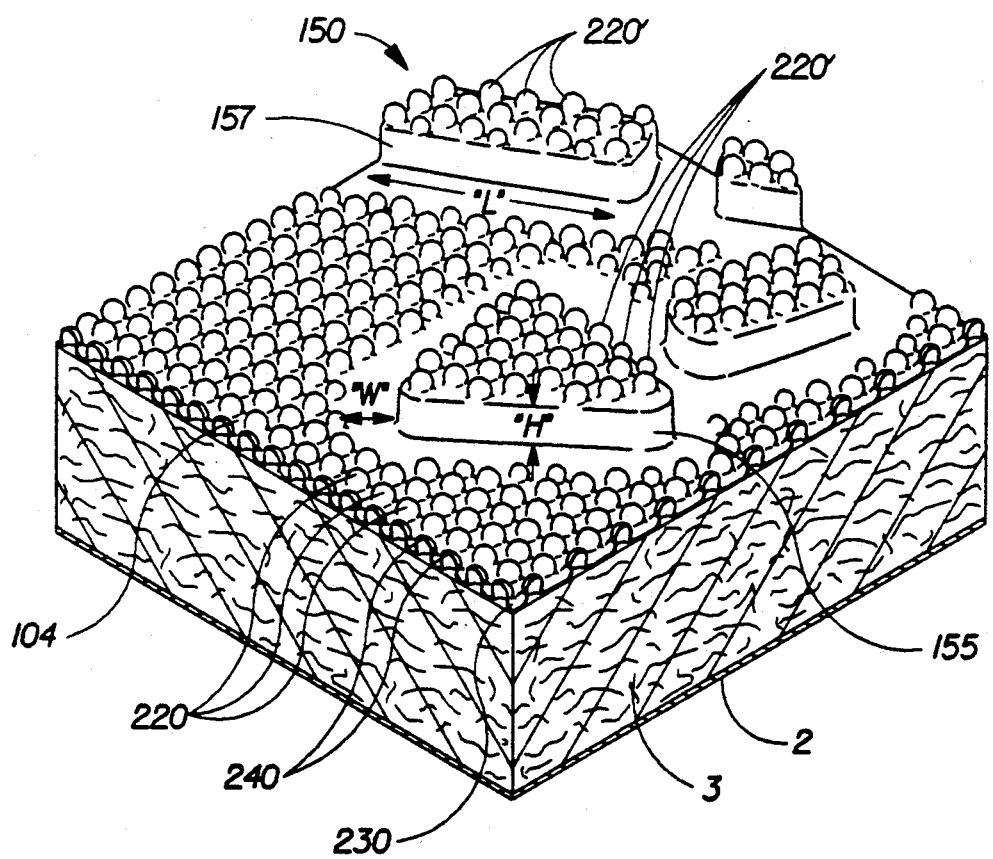
FIG. 5A is a greatly enlarged segment taken at a point corresponding to inset 5A in FIG. 4, said inset revealing the visually discernible pattern on the surface of said backsheet in much greater detail.

FIG. 5A is a view of a greatly enlarged segment of the diaper shown in FIG. 4, said view being taken at a point corresponding to inset 5A in FIG. 4.

As can be seen from FIG. 5A, the fluid-pervious topsheet 2 and absorbent core 3 employed in single use diaper 101 are generally similar to those employed with respect to diaper 1 shown in FIGS. 1 and 2. However, substantially fluid-impervious microbubbled backsheet 104 comprises only a single polymeric layer. In particular, the microbubbled backsheet 104 shown generally in FIG. 5A exhibits a pattern of discrete surface aberrations 220, which are not individually discernible to the normal naked eye when the perpendicular distance between the plane of the web and the observer's eye is at least about 12 inches. Each surface aberration 220 has a base portion 230 and a thinned microbubbled portion 240 located at a point substantially coinciding with its maximum amplitude. The microbubble 240 of the surface aberration comprises a highly flexible, substantially fluid-impervious, continuous membrane which is very much thinner than the base portion 230 of the surface aberration to which it is joined about its periphery. The microbubble 240 exhibits a maximum internal cross-sectional area, as measured in its fully expanded condition in a first plane oriented perpendicular to the amplitude of the surface aberration, which is greater than the minimum internal cross-sectional area of the relatively thicker base portion to which it is continuously joined about its periphery. Like the microaperture 125 in each surface aberration 120 of web 7 shown in FIG. 3A, microbubble 240 creates a discontinuity which reduces the resistance to compression and shear of each surface aberration 220, as well as the overall flexural rigidity of the polymeric web 104.

The reduced resistance to compression and shear of each of the surface aberrations 220 provides that surface of the web containing said microbubbles 240 with a tactile impression which is generally perceived as soft and cloth-like, while the reduced overall flexural rigidity of the web 104 minimizes the ability of the web to generate noise when it is subjected to movement. Substantially fluid-impervious webs of this general type and methods and apparatus for producing them are fully described in commonly assigned U.S. Pat. No. 4,846,821 issued to Lyons et al. on Jul. 11, 1989 and U.S. Pat. No. 4,778,644 issued to Curro et al. on Oct. 18, 1988, both of said patents being incorporated herein by reference.

As with the fluid-impervious microapertured composite backsheet 4 generally illustrated in FIG. 3A, the visually discernible pattern on the exposed surface of web 104 comprises a substantially planar, non-microbubbled portion of web 104 which is preferably located in the same plane in which at least a portion of the surface aberrations 220 originate. The substantially planar, non-microbubbled portion of web 104 comprises a regularly repeating pattern of boat anchors 150 generally similar to the regularly repeating pattern of boat anchors 50 shown in FIGS. 2 and 3A. The substantially planar, non-microbubbled portion of web 104 exhibits a width "W" equal to at least about 1½ times the normal center-to-center distance between adjacent surface aberrations 220, as measured in the microbubbled portions of the web located in the immediate vicinity of the visually discernible pattern of boat anchors 150. The substantially planar, non-microbubbled portion of the web 104 also exhibits a length "L" which extends continuously in a direction substantially perpendicular to its width "W". Together the width "W" and length "L" define a contrasting pattern which has an embossed appearance and which is visually discernible to the normal naked eye when the perpendicular distance between the observer's eye and the plane of the web is about 12 inches. As can be seen from FIG. 5A, the width "W" may be constant or may vary, as desired, along the length "L" of the pattern.

In the web embodiment illustrated in FIG. 5A, the continuously extending length "L" of the substantially planar, non-microbubbled portion of web 104 forms a halo or border comprising at least one closed loop, e.g., anchor tip 155, so as to completely isolate the microbubbled surface aberrations 220' contained within the closed loop from the otherwise identical microbubbled surface aberrations 220 surrounding the loop. In a particularly preferred embodiment, the visually discernible pattern comprises a multiplicity of such closed loops, e.g., anchor tip 155, central anchor portion 157, etc. In such case, the surface aberrations 220' contained within one closed loop are isolated not only from the surrounding surface aberrations 220, but also from the surface aberrations 220' contained within adjacent closed loops.

In a particularly preferred embodiment, the visually discernible pattern comprises a multiplicity of such closed loops arrayed in a regularly repeating decorative pattern. In the case of web embodiment 104, this pattern comprises a multiplicity of boat anchors 150. As with microapertured web 7 shown in FIGS. 2 and 3A, the embossed appearance of a microbubbled web 104 of the present invention can be further enhanced by positioning the surface aberrations 220' contained within the closed loops in a plane remote from the surface aberrations 220 surrounding the loops. In a particularly preferred embodiment, the surface aberrations 220' contained within closed loops 155, 157, etc., originate in a common plane which is located above the plane of the surface aberrations 220 surrounding the closed loops. Preferably, the two planes are separated from one another by a distance equal to at least about 1.0 times the amplitude of the surface aberrations 220 surrounding the closed loops to further enhance the embossed appearance of the web.

As with the composite substantially fluid-impervious backsheet embodiment 4 shown in FIGS. 2 and 3A, the substantially planar, non-microbubbled portions of web 104 which comprise the visually discernible pattern are preferably substantially smooth and will produce reflective gloss highlights which direct the observer's attention to the contrasting pattern imparted to the web 104 when it is struck by non-perpendicular incident light rays.

As will be appreciated by those skilled in the art, the same variations in pattern and methods of execution described in connection with microapertured polymeric web 7 of composite backsheet 4 shown in FIGS. 2 and 3A may be practiced with equal facility on microbubbled polymeric webs of the type generally disclosed in FIGS. 4 and 5A.

Figure 6:
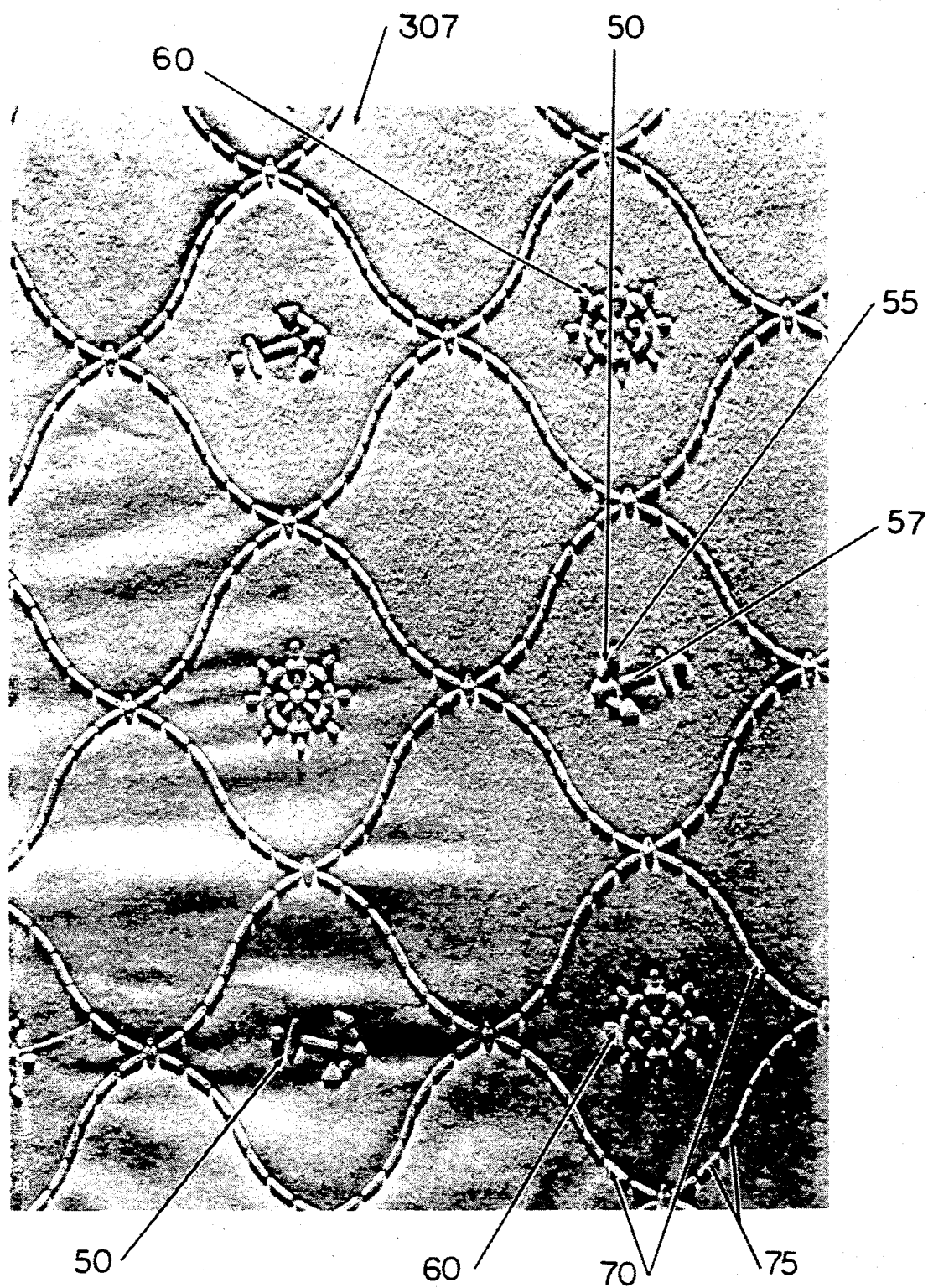
FIG. 6 is a highly enlarged plan view photograph of a microapertured polymeric web of the present invention, said web including a visually discernible pattern, said web being suitable for use as the exposed layer in a composite fluid-impervious backsheet of the type generally disclosed in FIGS. 2 and 3A.

FIG. 6 is a highly enlarged photograph, taken from directly overhead, of a microapertured polymeric web 307 of the present invention, said web being generally similar to microapertured polymeric web 7 illustrated in greatly enlarged condition in FIG. 3A. The visually discernible pattern in polymeric web 307 comprises, among other things, a multiplicity of regularly repeating boat anchors 50 of the type generally illustrated in Drawing FIGS. 2 and 3A. As can be seen from FIG. 6, each boat anchor 50 is itself made up of a multiplicity of closed loops, e.g., anchor tip 55, central anchor portion 57, etc., each closed loop being surrounded by a substantially planar, non-microapertured portion of the web. This is also true with respect to the regularly repeating pattern of pilot wheels 60 and the the continuously intersecting pattern of rope-like elements 70, each of which is made up of a multiplicity of relatively short closed loops 75 arranged in end-to-end curvilinear fashion.

Even at the greatly enlarged magnification shown in FIG. 6, the surface of the microapertured polymeric web 307 of the present invention appears very much like a fabric web having a distinctively embossed pattern on its exposed surface.

Figure 7:
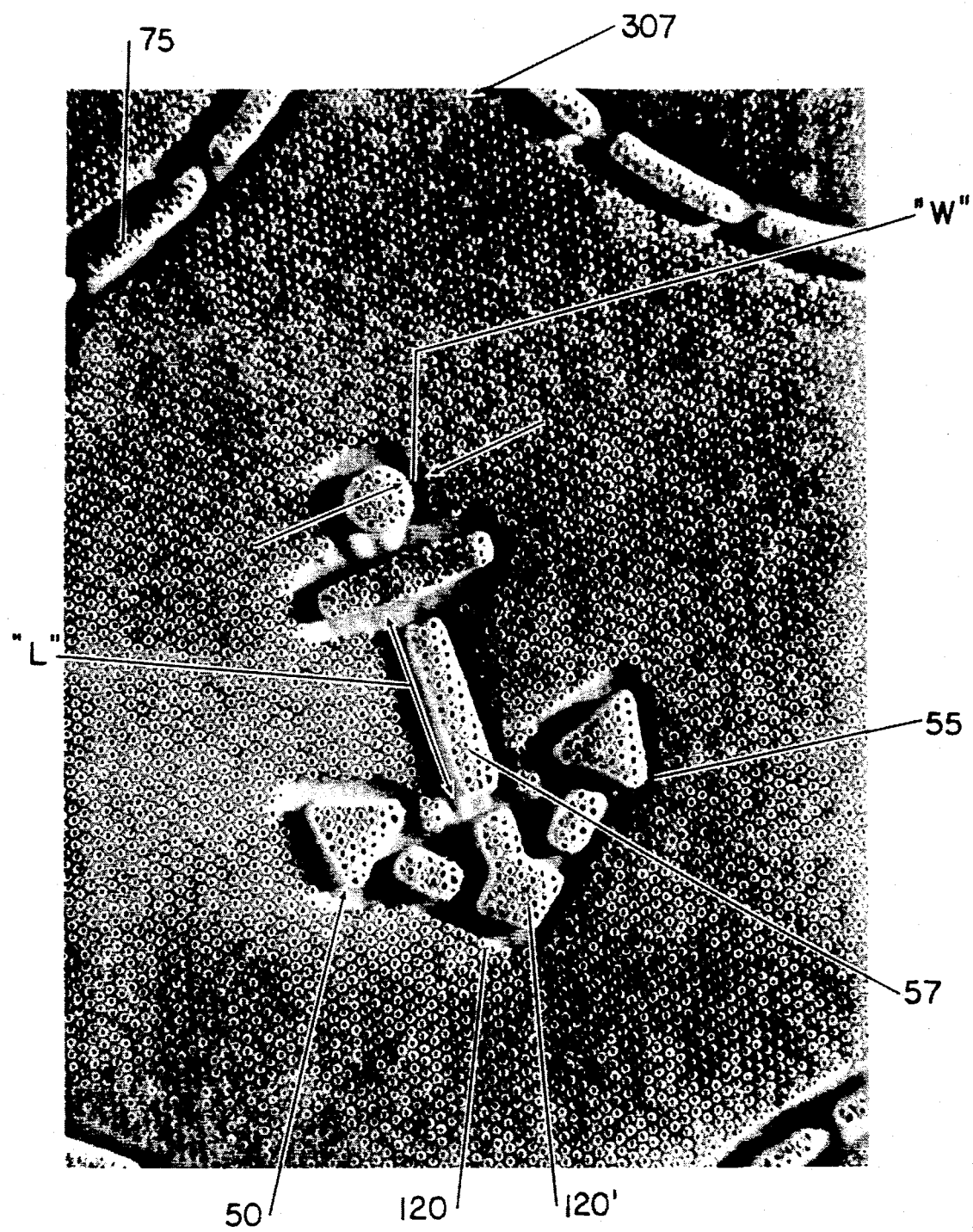
FIG. 7 is a further enlarged view of a particular portion of the microapertured polymeric web shown in FIG. 6, said view revealing in much greater detail the upwardly extending microapertured surface aberrations present throughout the surface of the web as well as the substantially planar, non-microapertured portion of the web which defines the visually discernible pattern in the web.

FIG. 7 is a further enlarged photograph, taken from directly overhead, of one of the boat anchors 50 comprising the contrasting visually discernible pattern in microapertured web 307. As can more readily be sen from the highly enlarged photograph of FIG. 7, the anchor 50 is made up of a multiplicity of closed loops, e.g., anchor tip 55, central anchor portion 57, etc., each closed loop being isolated from the surrounding microapertured surface aberrations 120 as well as from the microapertures surface aberrations 120' contained within adjacent closed loops by a substantially planar, non-microapertured portion of the web 307 having a width "W" and a length "L" extending continuously in a direction substantially perpendicular to its width.

In the web embodiment 307 illustrated in the greatly enlarged photograph of FIG. 7, the closed loops comprising each anchor 50, e.g., anchor tip 55, central anchor portion 57, etc., each contain microapertured surface aberrations 120' which are in a common plane located above the plane of the surrounding surface aberrations 120. Thus, the visual discernibility of the substantially planar, non-microapertured portion of the web is enhanced by the planar separation between the surface aberrations 120' contained within the closed loops 55, 57, etc., and the surrounding surface aberrations 120. This visual discernibility is enhanced even further by the shadows and the gloss highlights which result when the exposed surface of the web 307 is struck by non-perpendicular incident light rays.

Figure 8:
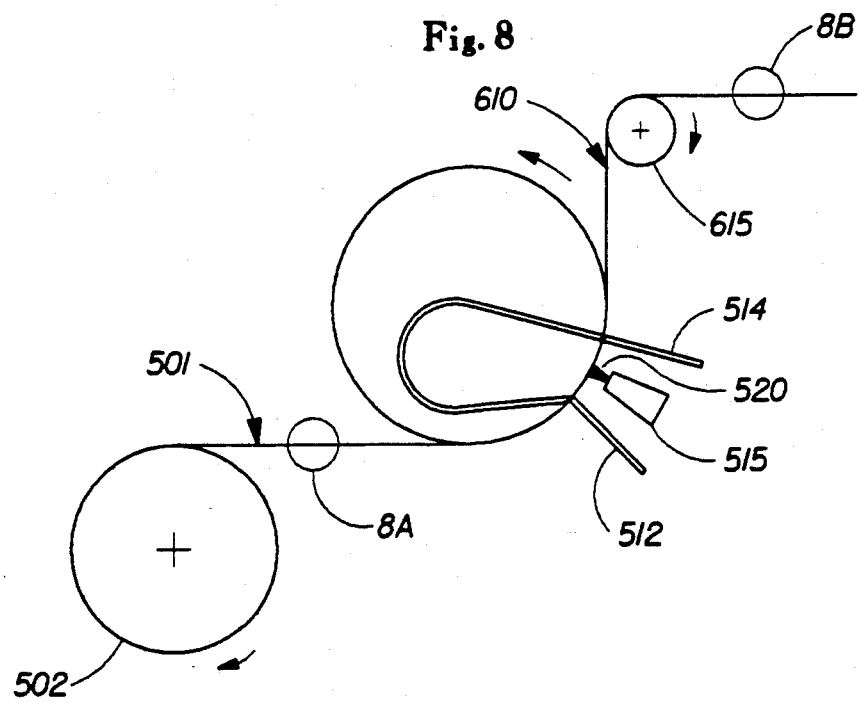
FIG. 8 is a simplified schematic illustration of a particularly preferred process for forming a microapertured web exhibiting a visually discernible pattern of the present invention.
Figure 8A:
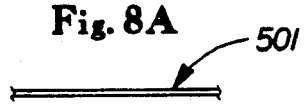
FIG. 8A is a highly enlarged, simplified cross-sectional illustration taken at a point corresponding to inset 8A in FIG. 8, said view revealing the substantially planar nature of the incoming web of unapertured polymeric film prior to processing by the apparatus disclosed in FIG. 8.

FIG. 8 is a simplified schematic illustration of a particularly preferred process for producing microapertured webs of the present invention, such as web 7 shown in Drawing FIG. 3A and web 307 shown in the photographs of FIGS. 6 and 7. In particular, a web of substantially smooth flat polymeric material 501, such as 1 mil thick polyethylene, is fed from a supply roll 502 onto the surface of a forming structure 505 of the present invention. The forming structure 505 rotates about a stationary vacuum chamber 510. The substantially planar unapertured cross-section of the incoming polymeric web 501 is shown in greatly enlarged form in the inset of FIG. 8A.

A high pressure liquid jet nozzle 515 is preferably directed at the exposed surface of the substantially smooth flat film 501 intermediate a pair of baffles 512, 514 as the polymeric web traverses the vacuum chamber. The high pressure, i.e., preferably at least about 560 N/cm$^2$ (800 psig), jet of liquid 520 causes the smooth flat polymeric web 501 to assume the general contour of the forming structure 505. In addition, because the forming structure 505 contains a multiplicity of apertures, the jet of liquid 520 causes localized deformation and rupture of those portions of the polymeric web 501 coinciding with the apertures in support member 505, thereby producing a microapertured web having a contrasting visually discernible pattern of the present invention in at least one of its surfaces.

The fully processed microapertured web, including the contrasting visually discernible pattern, is identified by reference numeral 610 in FIG. 8. A segment of the microapertured web 610 is shown in greatly enlarged form in the inset of FIG. 8B. The microapertured web 610 shown in FIG. 8B exhibits a multiplicity of fine-scale surface aberrations 620 generally similar to surface aberrations 120 of polymeric web 7 shown in FIG. 3A and of polymeric web 307 shown in FIGS. 6 and 7. The microapertures 625 in surface aberration 620, like microapertures 125 in surface aberrations 120, substantially coincide with the point of maximum amplitude of surface aberrations 620.

Figure 8B:
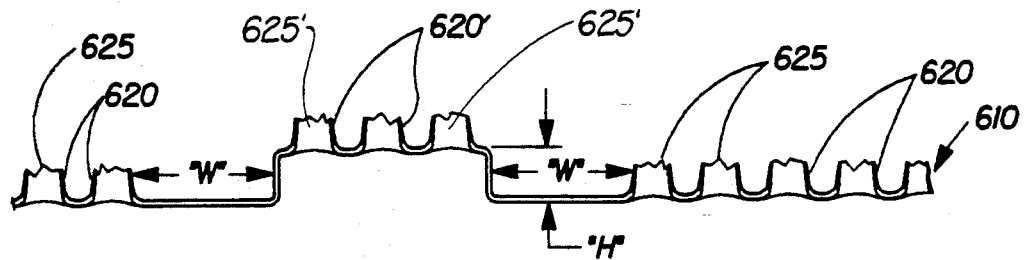
FIG. 8B is a highly enlarged, simplified cross-sectional illustration of a microapertured web exhibiting a visually discernible pattern of the present invention on its exposed surface after it exits the processing apparatus disclosed in FIG. 8, said cross-section being taken at a point corresponding to inset 8B in FIG. 8.

From FIG. 8B it can also be seen that microapertured surface aberration 620' having microapertures 625' corresponds generally to microapertured surface aberrations 120' having microapertures 125' in polymeric web 7 shown in FIG. 3A and polymeric web 307 shown in FIGS. 6 and 7. The microapertured surface aberration 620' are isolated from the surrounding surface aberration 620 by means of a substantially planar, non-microapertured portion of the polymeric web, said substantially planar, non-microapertured portion of the web having a width "W" and a length "L" (now shown) extending continuously in a direction substantially perpendicular to its width, thereby forming a halo or border comprising a multiplicity of closed loops. As can also be seen from FIG. 8B, the microapertured surface aberrations 620' contained within each closed loop formed by the substantially planar, non-microapertured portion of the web all originate in a plane located above the plane of the surrounding microapertured surface aberration 620. In particular, the two planes are separated by a vertical distance "H" which is preferably equal to at least about 1.0 times the amplitude of the surrounding surface aberrations 620.

More specific details as to the general nature of the process described in relation to FIG. 8 are disclosed in commonly assigned U.S. Pat. No. 4,629,643 issued to Curro et al. on Dec. 16, 1986, U.S. Pat. No. 4,609,518 issued to Curro et al. on Sep. 2, 1986 and U.S. Pat. No. 4,695,422 issued to Curro et al. on Sep. 22, 1987, all of said patents being hereby incorporated herein by reference. However, the forming structure 505 required to practice the present invention exhibits a number of critical features which are not disclosed in the aforementioned patents.

Figure 9:
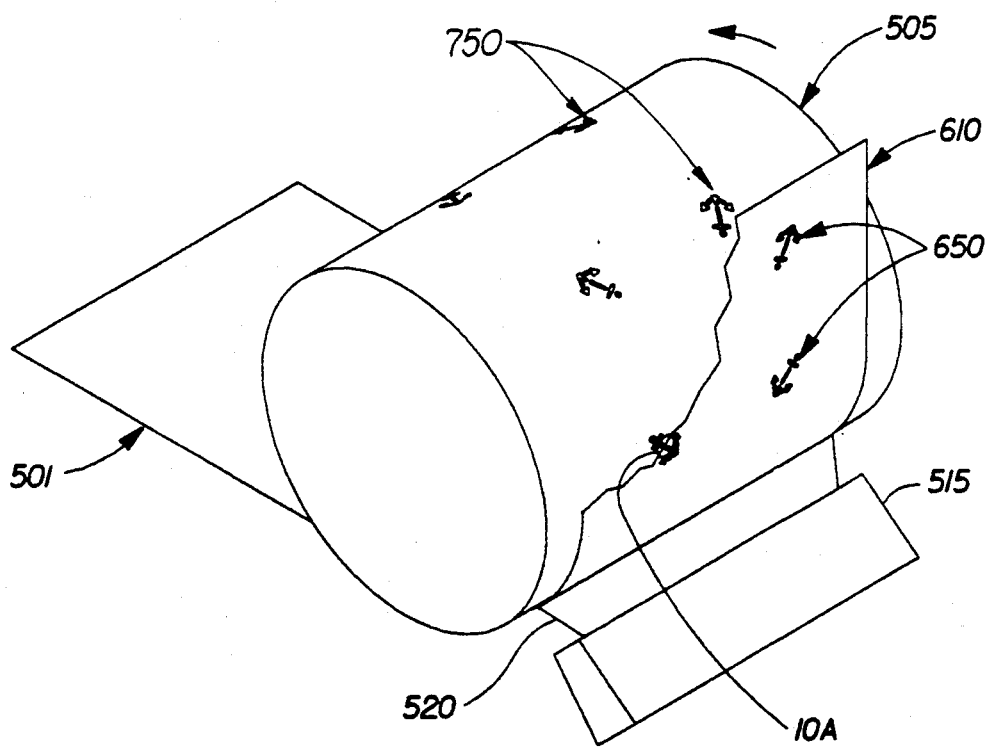
FIG. 9 is a greatly simplified perspective view of a cylindrical forming structure of the type used in the process of FIG. 8, said simplified perspective view showing the condition of the film after it has traversed the high pressure water jet illustrated in FIG. 8.

FIG. 9 is a simplified perspective illustration of a particularly preferred cylindrical forming structure 505 of the present invention shown with a portion of the fully processed polymeric web 610 still in contact with its surface. For simplicity, the web 610 exhibits a regularly repeating pattern comprising a multiplicity of boat anchors 650, which are generally similar to boat anchors 50 shown in connection with polymeric web 7 shown in FIG. 3A and polymeric web 307 shown in FIGS. 6 and 7. As can also be observed from FIG. 9, the boat anchors 650 in web 610 correspond to a similar pattern of boat anchors 750 included within cylindrical forming structure 505.

FIG. 10A is a highly enlarged, simplified schematic illustration taken through a portion of the forming structure 505 while the fully processed polymeric web 610 is still in contact with its surface, said view being taken at a point corresponding to inset 10A in FIG. 9. For ease of illustration the highly enlarged segment is shown in a planar rather than its true arcuate condition.

As can be seen from the greatly enlarged segment of FIG. 10A, forming structure 505 is preferably comprised of a multiplicity of laminar metallic sheets which are produced and assembled generally in accordance with the teachings of commonly assigned U.S. Pat. No. 4,342,314 issued to Radel et al. on Aug. 3, 1982 and hereby incorporated herein by reference. The lowermost portion of laminar forming structure 505 comprises a pair of identical sheets or layers 821 containing identical patterns of apertures 825 superposed on one another so that the apertures 825 precisely coincide with one another. The overlying pair of laminar sheets or layers 822, which are identical to one another, also contain a multiplicity of apertures 825 coinciding with a substantial number of the apertures 825 in underlying laminar sheets 821. However, laminar sheets 822 further contain non-apertured land areas 823 and 824 which produce substantially planar, non-microapertured areas in the finished web 610. In addition, laminar sheets 822 include relatively large open areas 826 adjacent land areas 823 and 824. These open areas 826 adjacent land areas 823 and 824 produce closed loops of microapertured surface aberrations 620' in the fully processed microapertured web 610. Because open areas 826 allow the polymeric web to make contact with one of the underlying laminar sheets 821 in laminate forming structure 505, the plane in which microapertured surface aberrations 620' within the closed loops originate is separated from the plane in which the surrounding microapertured surface aberrations 620 originate by a vertical wall having a height "H" corresponding to the total thickness of the two laminar sheets 822.

FIG. 11 depicts the exposed surface of microapertured web 610 of the present invention after the web segment shown in FIG. 10A has been stripped from the surface of forming structure 505 and inverted in the direction indicated by arrow 900, which connects FIGS. 10A and 11 with one another. As can be most readily seen in FIG. 11, the plane in which microapertured surface aberrations 620' originate is separated from the plane of the surrounding microapertured surface aberrations 620 by means of a vertical wall having an overall height "H" corresponding to the total thickness of laminar layers 822 in forming structure 505. As will be apparent from a review of FIGS. 8, 10A and 11, the initially planar, unapertured polymeric web 501 is caused to assume the three-dimensional contour as well as the aperture pattern of the forming structure 505 by means of the high pressure fluid jet 520 issuing from nozzle 515.

Figure 12:
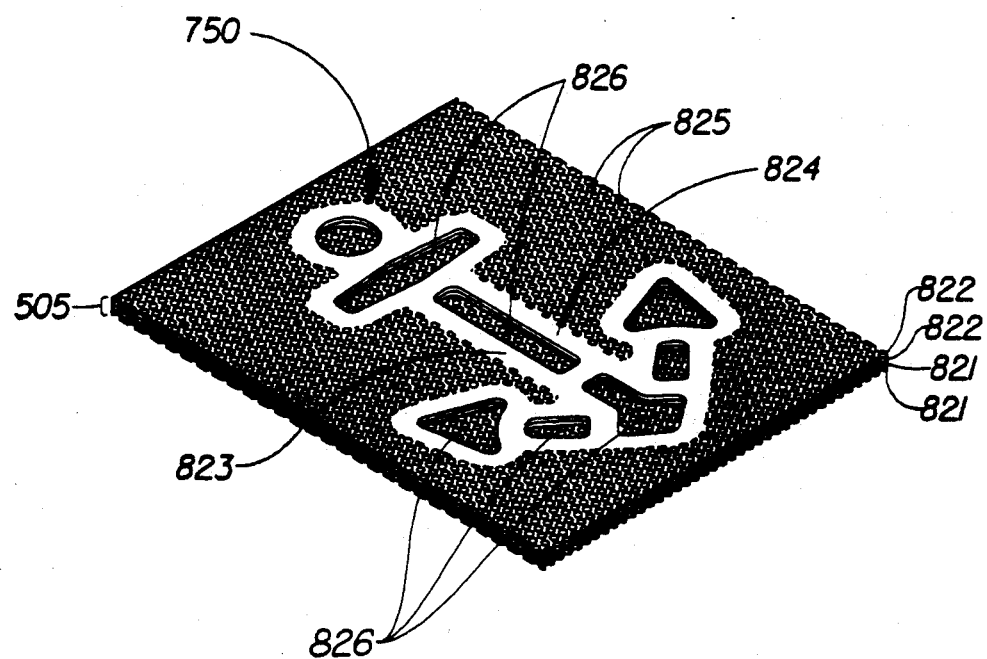
FIG. 12 is a highly enlarged, simplified schematic view of a portion of the laminate forming structure illustrated in FIG. 10A, said forming structure being shown in a planar rather than its true arcuate condition for ease of illustration.

FIG. 12 discloses a simplified segment of forming structure 505 including one complete boat anchor pattern 750. Although the segment of forming structure 505 illustrated in FIG. 12 is shown in planar condition, the superposed laminar layers 821, 821, 822, 822 will in actual fact be arcuate, since they comprise a portion of the continuous cylindrical surface generally illustrated in FIG. 9.

The simplified segment of forming structure 505 shown in FIG. 12 comprises a pair of laminar layers 821 including a multiplicity of apertures 825 secured in coinciding relation beneath a pair of laminar layers 822. In addition to a substantial number of coinciding apertures 825, layers 822 further include land areas 823 and 824 which correspond to the substantially planar, non-microapertured portions of the fully processed polymeric web 610. In addition, layers 822 include large open areas 826 which correspond to the closed loops of surface aberrations 620' formed in the fully processed polymeric web 610.

Figure 13:
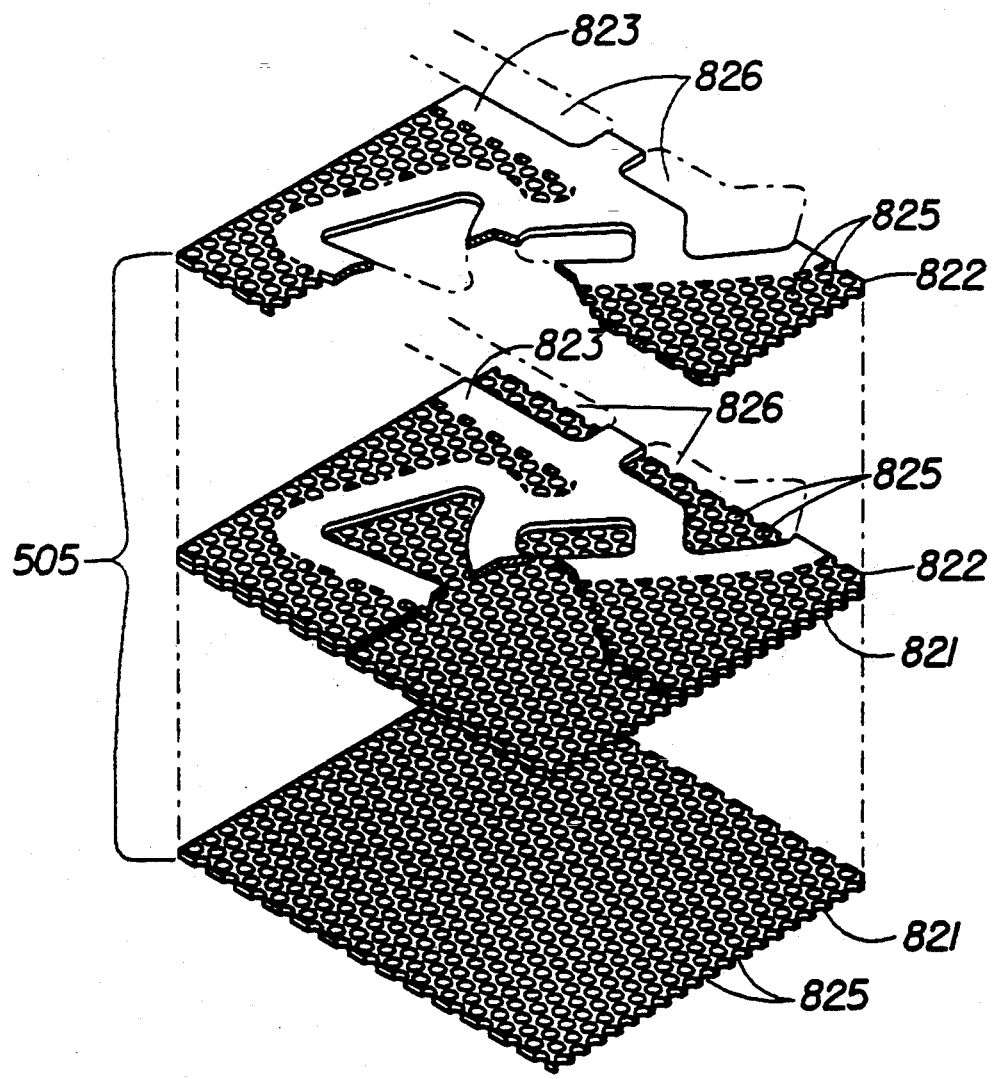
FIG. 13 is a further enlarged, partially exploded view of a portion of the laminate forming structure illustrated in FIG. 13.

FIG. 13 is a further enlarged, partially exploded view of a portion of the simplified segment of the laminar forming structure 505 illustrated in FIG. 12. The partially exploded view of FIG. 13 illustrates the manner in which the coinciding portions of the respective lamina 821, 821, 822, 822 are secured to one another to produce the desired three-dimensional contour in the fully processed polymeric web 610.

Figure 14:
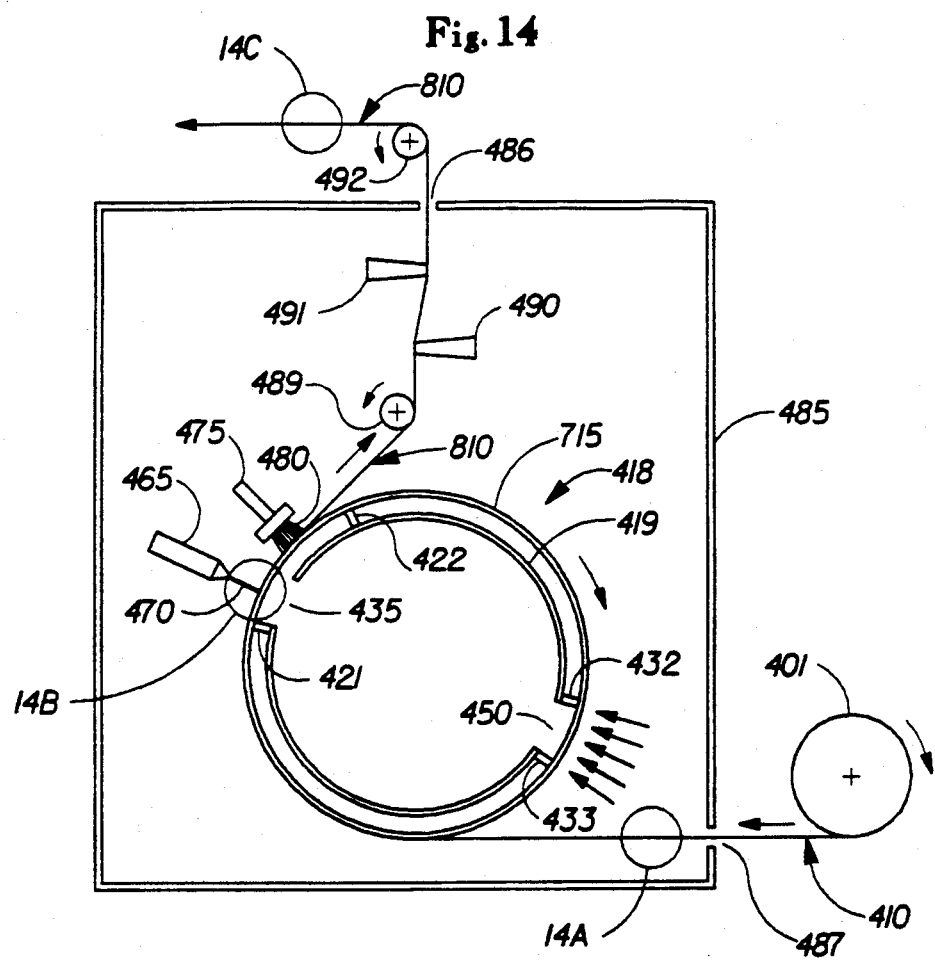
FIG. 14 is a simplified schematic illustration of a particularly preferred process for forming a microbubbled web exhibiting a visually discernible pattern of the present invention.

FIG. 14 is a simplified schematic illustration depicting a particularly preferred method for producing a substantially fluid-impervious, microbubbled polymeric web exhibiting a contrasting visually discernible pattern similar in many respects to that illustrated in FIG. 5A.

Figure 14A:
FIG. 14A is a highly enlarged, simplified cross-sectional view taken at a point corresponding to inset 14A in FIG. 14, said view revealing the substantially planar nature of the incoming web of unapertured polymeric film prior to processing by the apparatus disclosed in FIG. 14.

In the process embodiment shown in FIG. 14, a web of substantially planar, unapertured film 410 comprised of a polymeric material, such as polyethylene, is shown in the enlarged inset of FIG. 14A. The web 410 is preferably fed from a supply roll 401 through an inlet slot 487 in cabinet 485 and onto the surface of a forming drum 418 about which a forming structure 715 continuously rotates at substantially the same speed as the incoming web. The forming drum 410, which is contained within a housing 485, preferably includes an internally located vacuum chamber 419 which is preferably stationary relative to the moving forming structure 715. A pair of stationary vacuum seals 421, 422 approximately coinciding with the beginning and end, respectively, of the vacuum chamber's first inlet 435 are used to establish a seal between the innermost surface of the rotating forming structure 715 and the first vacuum chamber inlet 435. An additional pair of seals 432, 433 establish a similar seal between the innermost surface of the rotating forming structure 715 and a second vacuum chamber inlet 450. The second vacuum chamber inlet 450 is positioned in an area of the forming drum 418 where it will not be blocked by the web of film 410.

Opposite the first vacuum chamber inlet 435 there is preferably provided means for applying a fluid pressure differential to the substantially planar web of polymeric film 410 as it traverses the area of the forming drum intermediate vacuum seals 421, 422. In the illustrated embodiment, the fluid pressure differential applicator means comprises a high pressure liquid nozzle 465 which discharges a jet of high pressure liquid 470, such as water, substantially uniformly across the entire width of the moving polymeric web 410, thereby converting it from a substantially planar condition to a microbubbled web 810 having a visually discernible pattern in at least one of its surfaces. The water is preferably applied at a pressure of at least about 350 N/cm$^2$ (500 psig), most preferably at least about 700 N/cm$^2$ (1,000 psig). The water is also preferably applied at an elevated temperature which is below the transformation temperature range of the incoming polymeric web 410 so that the web remains in a substantially solid state throughout the entire process. This preserves the physical properties and thermomechanical history of the incoming web. A water cooling spray 480 is preferably applied to the processed web 810 by a secondary low pressure nozzle 475 after the web has been transformed from its substantially planar condition.

The fully processed web thereafter passes between a pair of water wiping blades 490, 491 to remove excess water and out discharge slot 486 in cabinet 485 as it travels between idler rolls 489, 492.

Details as to the effects of varying the water temperature and the preferred construction and positioning for high pressure liquid nozzle 465 are set forth in commonly assigned U.S. Pat. No. 4,778,644 issued to Curro et al. on Oct. 18, 1988 and hereby incorporated herein by reference.

FIG. 14B is a highly enlarged, simplified cross-section showing the effect of high pressure liquid jet 470 on the substantially planar, unapertured web of polymeric film 410, said cross-section being taken at a point corresponding to inset 14B in FIG. 14. As can be seen from FIG. 14B, the laminar forming structure 715 comprises a pair of identical laminar sheets 922 containing coinciding patterns of tiny apertures 925 superposed upon an underlying porous layer 707. The coinciding apertures 925 in laminar sheets 922 produce the base portions 430 of the microbubbled surface aberrations 420 in the fully processed web 810. The unapertured land areas 923 and 924 in laminar sheets 922 produce the substantially planar non-microbubbled portions of width "W" in the fully processed web 810.

Underlying porous layer 707 exhibits a much finer degree of porosity than either of the outermost laminar sheets 922 utilized in the outermost portion of laminar forming structure 715. As will be appreciated by those skilled in the art, laminar sheets 922 and porous underlying member 707 must be secured to one another so as to avoid either plugging the tiny apertures 925 in the laminar sheets 922 or substantially reducing the porosity of the underlying support member 707.

With respect to the porosity of underlying support member 707, it has been learned that is the interstitial openings formed between the intersecting filaments in porous layer 707 are between about 0.5 mils and about 1.0 mils, then the underlying porous layer 707 will allow venting of any air trapped between the plastic web 410 and the outermost laminar sheets 922, yet will provide enough support to the polymeric web to substantially prevent rupturing of the thin portions of the web ultimately comprising the highly thinned microbubbles 440 in surface aberrations 420.

In a particularly preferred embodiment, porous layer 707 is comprised of a woven wire mesh. The woven wire mesh is preferably comprised of filaments having a diameter of about 3 mils (0.003") or less and a mesh count between about 165 filaments per lineal inch by about 800 filaments per lineal inch and about 325 filaments per lineal inch by about 2,300 filaments per lineal inch in a twilled Dutch weave pattern (there is a degree of filament overlap with this pattern).

More specific details as to the overall construction of laminate forming structure 715 and the porosity and support requirements for the underlying porous layer are set forth in the aforementioned commonly assigned U.S. Pat. No. 4,778,644 issued to Curro et al. on Oct. 18, 1988 and incorporated herein by reference.

As with the web embodiments disclosed earlier herein, the substantially planar, non-microbubbled portions of the web show in FIG. 14B exhibit a width "W" which is preferably at least about 1½ times the center-to-center distance between adjacent microbubbled surface aberrations 420, as measured in the immediate vicinity of the visually discernible pattern.

Figure 14C:
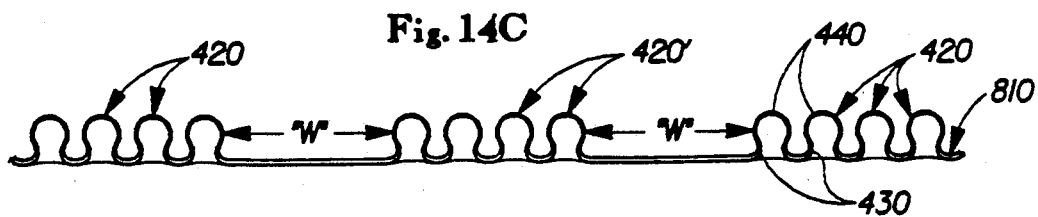
FIG. 14C is a highly enlarged, simplified cross-sectional illustration of a microbubbled web exhibiting a visually discernible pattern of the present invention on its exposed surface after it exits from the processing apparatus disclosed in FIG. 14, said cross-section being taken at a point corresponding to inset 14B in FIG. 14.

FIG. 14C is a highly enlarged, simplified, cross-sectional schematic of a fully processed microbubbled web 810 of the present invention, said view being taken at a point corresponding to inset 14C in FIG. 14. The web shown in FIG. 14C is similar in many respects to the microbubbled web 140 shown generally in FIG. 5A, with the exception that the microbubbled surface aberrations 420' located within the closed loops formed by the substantially planar, non-microbubbled portions of the web are located in the same plane as the surrounding microbubbled surface aberrations 420. If desired, the closed loops of microbubbled surface aberration 420′ may, of course, by made to originate in a plane located either above or below the plane in which the surrounding surface aberrations 420 originate. In the latter event construction of the laminate forming structure 715 must be adjusted, as required, to produce the desired three-dimensional contour in the fully processed web.

Figure 15:
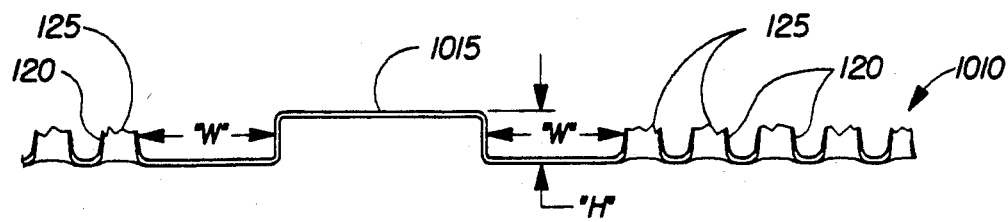
FIGS. 15, 16 and 17 are simplified cross-sectional illustrations of alternative embodiments of microapertured webs, each of said webs exhibiting a visually discernible pattern of the present invention on its exposed surface.
Figure 16:
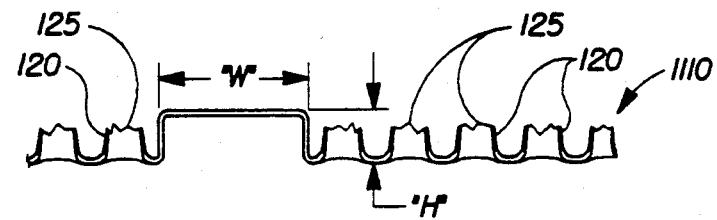
Figure 17:
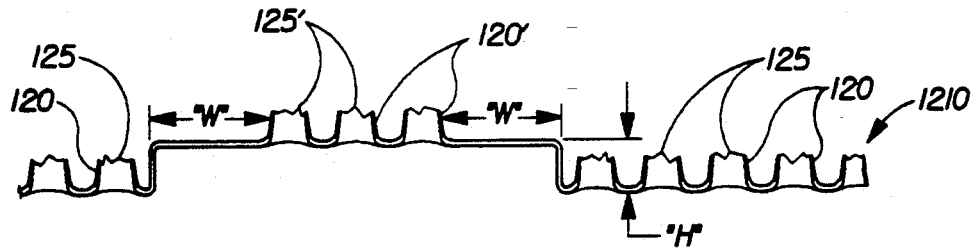

FIGS. 15, 16 and 17 are simplified cross-sectional illustrations of still other web embodiments which are within the scope of the present invention.

Microapertured web embodiment 1010 shown in FIG. 15 exhibits a pattern of microapertured surface aberrations 120 extending substantially across its surface. Each microapertured surface aberration 120 includes a microaperture 125 substantially coinciding with its point of maximum amplitude. As with the microapertured web embodiment 610 illustrated in FIG. 8B, web embodiment 1010 includes a non-microapertured, horizontally oriented portion having a width "W" and a length "L" (not shown) extending continuously in a direction substantially perpendicular to its width. Together the width "W" and length "L" form a halo or border comprising a multiplicity of closed loops 1015.

However, closed loop 1015 in web embodiment 1010 does not include any microapertured surface aberrations. Rather, it comprises a substantially planar surface which may, if desired, be similar to the substantially planar, non-microapertured, horizontally oriented portion of the web of width "W" and length "L" (not shown) surrounding area 1015. If substantially planar surface 1015 is glossy, the resulting web will exhibit a substantially cloth-like visual and tactile impression in the areas where microapertured surface aberrations 120 are present and an embossed glossy pattern comprised of closed loops 1015, each surrounded by a substantially planar portion of width "W" and length "L" (not shown).

In the web embodiment 1010 shown in FIG. 15, the plane containing closed loop 1015 is separated from the plane in which surface aberrations 120 originate by a vertical distance "H" which is preferably equal to at least about 1.0 times the amplitude of the surrounding surface aberrations 120.

Web embodiment 1110 shown in FIG. 16 is somewhat similar to web embodiment 810 shown in FIG. 14C. However, the surface aberrations 120 each include a microaperture 125 at their point of maximum amplitude in web embodiment 1110, while the surface aberrations 420 in web embodiment 810 each exhibit a microbubble 440 at their point of maximum amplitude. In addition, the substantially planar, non-microapertured, horizontally oriented portion of web 1110 comprising the visually discernible pattern, which has a width "W" and a length "L" (not shown), is located in a second plane above the plane in which surface aberrations 120 originate. In particular, the two planes are separated by a vertical distance "H" which is preferably equal to at least about 1.0 times the amplitude of the surrounding surface aberrations 120.

FIG. 17 discloses still another web embodiment 1210 of the present invention. Web embodiment 1210 is generally similar to web embodiment 610 shown in FIG. 8B, with the exception that the substantially planar, non-microapertured, horizontally oriented portion of web 1210 comprising the visually discernible pattern, which has a width "W" and a length "L" (now shown), is located in the plane of surface aberrations 120′ rather than in the plane of the surrounding surface aberrations 120. As with web embodiments 1010 and 1110, the two planes are separated by a vertical distance "H" which is preferably equal to at least about 1.0 times the amplitude of the surrounding surface aberrations 120.

As will be appreciated by those skilled in the art, webs of the present invention may be executed in fluid-pervious microapertured versions, fluid-impervious microbubbled versions and fluid-impervious microapertured composite versions. Alternatively, webs of the aforementioned type may be rendered fluid-pervious only in predetermined locations. Furthermore, webs of the present invention employing both microapertured surface aberrations and microbubbled surface aberrations may be produced.

From the description contained herein, it is clear that microapertured and microbubbled webs exhibiting contrasting visually discernible patterns of the present invention exhibit a unique combination of characteristics and benefits which are neither taught nor suggested by the prior art.

While the present invention has been described primarily in the context of a fluid-impervious backsheet for a single use absorbent bandage such as a diaper, it is recognized that the present invention may also be practiced to advantage in many other applications and environments. It will be obvious to those skilled in the art that various changes and modifications can be made without departing from the spirit and scope of the invention, and it is intended to cover in the appended claims all such modifications that are within the scope of this invention.

What is claimed is:

1. A microapertured polymeric web exhibiting a soft and silky tactile impression as well as a contrasting visually discernible pattern on at least one surface thereof, said silky feeling surface of said web exhibiting a pattern of discrete surface aberrations which are not individually discernible to the normal naked eye when the perpendicular distance between said web and the observer's eye is at least about 12 inches, the density of said surface aberrations being at least about 3,600 per square inch, the center-to-center distance between adjacent surface aberrations not exceeding about 25 mils, each of said surface aberrations having its amplitude oriented substantially perpendicular to the surface in which said surface aberration originates and exhibiting a maximum cross-sectional dimension not exceeding about 20 mils, as measured perpendicular to its amplitude, the end of each of said surface aberrations further including at least one microaperture substantially coincidental with its point of maximum amplitude, said microaperture exhibiting a multiplicity of thin, irregularly shaped petals about its periphery, said microaperture further creating a discontinuity which reduces the resistance to compression and shear of each of said surface aberrations as well as the degree of contact with the observer's skin, whereby the overall tactile impression of that surface of said web containing the microapertured portions of said surface aberrations is perceived as generally soft and silky, said contrasting visually discernible pattern comprising a substantially planar, non-microapertured, horizontally oriented portion of said web, said substantially planar, non-microapertured, horizontally oriented portion of said web having a width "W" equal to at least about 1½ times the normal center-to-center distance between adjacent surface aberrations, as measured in the microapertured portions of aid web in the immediate vicinity of said visually discernible pattern, and a length "L" extending continuously in a direction substantially perpendicular to said width, said substantially planar, non-microapertured, horizontal portion of said web of width "W" and length "L" being located in a plane which is positioned no lower than the plane in which at least a portion of said microapertured surface aberrations in said web originate, said width "W" and said length "L" together defining a contrasting pattern which is visually discernible to the normal naked eye when the perpendicular distance between the observer's eye and the plane of said web is about 12 inches.

2. The web of claim 1, wherein said substantially planar, non-microapertured portion of said web having a width "W" and a length "L" is located in the same plane in which at least a portion of said microapertured surface aberrations in said web originate.

3. The web of claim 2, wherein said substantially planar, non-microapertured portion of said web having a width "W" and a length "L" is located in the same plane in which the majority of said microapertured surface aberrations in said web originate.

4. The web of claim 1, wherein the continuously extending length "L" of said substantially planar, non-microapertured portion of said web comprising said visually discernible pattern forms at least one closed loop located in a plane remote from the plane of said substantially planar, non-microapertured portion of said web, thereby completely isolating the surface contained within said loop from the surface aberrations surrounding said loop.

5. The web of claim 4, wherein said surface contained within said loop also exhibits a pattern of discrete surface aberrations which are not individually discernible to the normal naked eye when the perpendicular distance between said web and the observer's eye is at least about 12 inches.

6. The web of claim 5, wherein each of said surface aberrations contained within said loop includes at least one microaperture substantially coincidental with its point of maximum amplitude.

7. The web of claim 4, claim 5, or claim 6, wherein said contrasting visually discernible pattern comprises a multiplicity of said closed loops.

8. The web of claim 7, wherein said contrasting visually discernible pattern comprises a regularly repeating pattern.

9. The web of claim 5, wherein the surface aberrations contained within said loop are of a dissimilar size from the surface aberrations surrounding said loop.

10. The web of claim 5 or claim 6, wherein the surface aberrations contained within said closed loop originate in a plane located above the plane of said surface aberrations surrounding said closed loop.

11. The web of claim 10, wherein the plane of said surface aberrations contained within said closed loop is separated from the plane of said surface aberrations surrounding said closed loop by a distance equal to at least 1.0 times the amplitude of said surface aberrations surrounding said closed loop.

12. The web of claim 1, wherein said substantially planar, non-microapertured portion of said web comprising said contrasting visually discernible pattern is substantially smooth and will produce a reflective gloss highlight when struck by incident light rays, thereby enhancing the visual discernibility of said pattern.

13. The web of claim 1, further including a substantially liquid-impervious layer secured in juxtaposed relation adjacent the surface of said web which does not contain said microapertured surface aberrations to render said microapertured web substantially impervious to the passage of fluid.

14. The web of claim 14, wherein said liquid impervious layer comprises a continuous coating applied to said microapertured web.

15. A substantially fluid-impervious, microbubbled polymeric web exhibiting a contrasting visually discernible pattern, said web exhibiting very low levels of noise when subjected to movement as well as a soft and cloth-like tactile impression on at least one of its surfaces, said cloth-like surface of said web exhibiting a pattern of discrete surface aberrations, each of said surface aberrations having its amplitude oriented substantially perpendicular to the surface in which said surface aberration originates, each of said surface aberrations exhibiting a maximum cross-sectional dimension of about 25 mils or less, as measured in a plane oriented perpendicular to the amplitude of said surface aberration with the microbubble in its fully expanded condition, each of said surface aberrations having a base portion and an end portion, the end portion of each of said surface aberrations comprising at least one microbubble substantially coinciding with the point of maximum amplitude of the surface aberration to which it is continuously joined about its periphery, said microbubble comprising a highly flexible, substantially fluid-impervious, continuous membrane which is very much thinner than the base portion of said surface aberration, said microbubble further exhibiting a maximum internal cross-sectional area, as measured in its fully expanded condition in a first plane oriented perpendicular to the amplitude of said surface aberration, which is greater than the minimum internal cross-sectional area of said relatively thicker base portion to which it is continuously joined about its periphery, as measured in a second plane oriented parallel to said first plane, said microbubble creating a discontinuity which reduces the resistance to compression and shear of said surface aberration as well as the overall flexural rigidity of said web, whereby said reduced resistance to compression and shear of each of said surface aberrations provides that surface of said web containing said microbubbles with a tactile impression which is generally perceived as soft and cloth-like while the reduced overall flexural rigidity of aid web minimize the ability of said web to generate nose when said web is subjected to movement, said contrasting visually discernible pattern comprising a substantially planar, non-microbubbled, horizontally oriented portion of said web, said substantially planar, non-microbubbled, horizontally oriented portion of said web having a width "W" equal to at least about 1½ times the normal center-to-center distance between adjacent surface aberrations, as measured in the microbubbled portions of said web in the immediate vicinity of said visually discernible pattern, and a length "L" extending continuously in a direction substantially perpendicular to its width, said substantially planar, non-microbubbled, horizontally oriented portion of said web of width "W" and length "L" being located in a plane which is positioned no lower than the plane in which at least a portion of said microbubbled surface aberrations in aid web originate, said width "W" and said length "L"

together defining a contrasting pattern which is visually discernible to the normal naked eye when the perpendicular distance between the observer's eye and the plane of said web is about 12 inches.

16. The web of claim 15, wherein said substantially planar, non-microbubbled portion of said web having a width "W" and a length "L" is located in the same plane in which at least a portion of said microbubbled surface aberrations in said web originate.

17. The web of claim 16, wherein said substantially planar, non-microbubbled portion of said web having a width "W" and a length "L" is located in the same plane in which the majority of said microbubbled surface aberrations in said web originate.

18. The web of claim 15, wherein the length "L" of said substantially planar, non-microbubbled portion of said web comprising said visually discernible pattern forms at least one closed loop located in a plane remote from the plane of said substantially planar, non-microbubbled portion of said web, thereby completely isolating the surface contained within said loop from the surface aberrations surrounding said loop.

19. The web of claim 18, wherein said surface contained within said loop also exhibits a pattern of discrete surface aberrations which are not individually discernible to the normal naked eye when the perpendicular distance between said web and the observer's eye is at least about 12 inches.

20. The web of claim 19, wherein each of said surface aberrations contained within said loop includes at least one microbubble substantially coincidental with its point of maximum amplitude.

21. The web of claim 18, claim 19 or claim 20, wherein said contrasting visually discernible pattern comprises a multiplicity of said closed loops.

22. The web of claim 21, wherein said contrasting visually discernible pattern comprises a regularly repeating pattern.

23. The web of claim 19, wherein the surface aberrations contained within said loop are of a dissimilar size from the surface aberrations surrounding said loop.

24. The web of claim 19 or claim 20, wherein the surface aberrations contained within said closed loop originate in a plane located above the plane of said surface aberrations surrounding said closed loop.

25. The web of claim 24, wherein the plane of said surface aberrations contained within said closed loop is separated from the plane of said surface aberrations surrounding said closed loop by a distance equal to at least 1.0 times the amplitude of said surface aberrations surrounding said closed loop.

26. The web of claim 15, wherein said substantially planar, non-microbubbled portion of said web comprising said contrasting visually discernible pattern is substantially smooth and will produce a reflective gloss highlight when struck by incident light rays, thereby enhancing the visual discernibility of said pattern.

* * * * *

UNITED STATES PATENT AND TRADEMARK OFFICE
CERTIFICATE OF CORRECTION

PATENT NO. : 5,158,819

DATED : October 27, 1992

INVENTOR(S) : W. H. Goodman, Jr., W. I. Mullane, Jr., B. F. Perry, G. G. Trout

It is certified that error appears in the above-identified patent and that said Letters Patent is hereby corrected as shown below:

```
Column 1, line 58, "ar" should read -- art -- .
Column 2, line 3, "disclosed" should read -- discloses -- .
Column 2, line 24, "patient" should read -- patent -- .
Column 2, line 27, "patient" should read -- patent -- .
Column 2, line 29, "minimize" should read -- minimizes -- .
Column 2, line 40, "disclosed" should read -- discloses -- .
Column 2, line 63, "ib" should read -- is -- .
Column 3, line 48, "aberrations's" should read -- aberrations -- .
Column 9, line 51, "disclosed" should read -- discloses -- .
Column 12, line 13, "sen" should read -- seen -- .
Column 12, line 19, "microapertures" should read -- microapertured -- .
Column 13, line 22, "now" should read -- not -- .
Column 15, line 22, "410" should read -- 418 -- .
Column 16, line 29, "is" should read -- if -- .
Column 16, line 66, "140" should read -- 104 -- .
Column 19, line 4, "aid" should read -- said -- .
Column 20, line 50, "aid" should read -- said -- .
Column 20, line 51, "nose" should read -- noise -- .
Column 20, line 67, "aid" should read -- said -- .
```

Signed and Sealed this

Thirteenth Day of April, 1993

Attest:

STEPHEN G. KUNIN

Attesting Officer     Acting Commissioner of Patents and Trademarks